US008517016B2

(12) United States Patent
Caro et al.

(10) Patent No.: US 8,517,016 B2
(45) Date of Patent: Aug. 27, 2013

(54) METHOD OF DETERMINING LUNG CONDITION INDICATORS

(75) Inventors: Richard G. Caro, San Francisco, CA (US); Noam Gavriely, Haifa, IL (US)

(73) Assignee: Pulmosonix Pty Ltd., Elsternwick, Victoria (AU)

( * ) Notice: Subject to any disclaimer, the term of this patent is extended or adjusted under 35 U.S.C. 154(b) by 1128 days.

(21) Appl. No.: 12/342,186

(22) Filed: Dec. 23, 2008

(65) Prior Publication Data
US 2009/0171231 A1 Jul. 2, 2009

Related U.S. Application Data

(63) Continuation-in-part of application No. 11/116,667, filed on Apr. 27, 2005, now abandoned.

(51) Int. Cl.
*A61M 16/00* (2006.01)
*A62B 7/00* (2006.01)
*A61B 7/00* (2006.01)
*A61B 5/08* (2006.01)

(52) U.S. Cl.
USPC ............ 128/204.23; 128/204.18; 128/200.24; 600/586; 600/538; 600/532; 600/529

(58) Field of Classification Search
USPC ............. 128/200.24, 200.26, 204.23, 207.14, 128/207.15, 898; 600/484, 586, 528–543, 600/552, 561
See application file for complete search history.

(56) References Cited

U.S. PATENT DOCUMENTS

| 3,990,435 | A | | 11/1976 | Murphy |
| 4,009,616 | A | | 3/1977 | Wonn |
| 4,094,304 | A | | 6/1978 | Wright, Jr. |
| 4,115,356 | A | | 9/1978 | Hilliard |
| 4,140,281 | A | | 2/1979 | Fulghum et al. |
| 4,155,356 | A | | 5/1979 | Venegas |
| 4,173,897 | A | | 11/1979 | Forstermann et al. |
| 4,197,856 | A | | 4/1980 | Northrop |
| 4,240,281 | A | | 12/1980 | Lather et al. |
| 4,306,567 | A | | 12/1981 | Krasner |
| 4,326,416 | A | | 4/1982 | Fredberg |
| 4,424,815 | A | * | 1/1984 | Kuntz ........................... 600/528 |
| 4,653,327 | A | | 3/1987 | Vertarasian et al. |

(Continued)

FOREIGN PATENT DOCUMENTS

| CA | 2262236 | 8/1999 |
| EP | 0371424 A1 | 11/1989 |

(Continued)

OTHER PUBLICATIONS

Murphy, R., et al. "Lung Sound Patterns in Common Pulmonary Disorders" —Faulkner Hospital, Boston, MA.

(Continued)

*Primary Examiner* — Annette Dixon
(74) *Attorney, Agent, or Firm* — Greenberg Traurig LLP; Cecily Anne O'Regan

(57) ABSTRACT

A method and a microprocessor controlled device for use in medical evaluation of the pulmonary system. The method and device incorporate two different non invasive evaluative techniques. Passive auscultation provides indicators of lung condition. Active auscultation, a different evaluative technique, provides information or indications generally not available or provided from passive auscultation. Combining the information from both techniques greatly improves the ability to provide effective medical treatment.

19 Claims, 8 Drawing Sheets

(56) References Cited

U.S. PATENT DOCUMENTS

| | | | |
|---|---|---|---|
| 4,671,295 A | 6/1987 | Abrams et al. | |
| 4,672,977 A | 6/1987 | Kroll | |
| 4,705,048 A | 11/1987 | Pfohl | |
| 4,706,229 A | 11/1987 | Congdon | |
| 4,830,015 A | 5/1989 | Okazaki | |
| 4,951,678 A | 8/1990 | Joseph et al. | |
| 4,982,738 A | 1/1991 | Griebel | |
| 5,010,889 A * | 4/1991 | Bredesen et al. | 600/528 |
| 5,058,600 A | 10/1991 | Schechter et al. | |
| 5,134,995 A | 8/1992 | Gruenke et al. | |
| 5,143,078 A | 9/1992 | Mather et al. | |
| 5,165,417 A * | 11/1992 | Murphy, Jr. | 600/529 |
| 5,213,108 A | 5/1993 | Bredesen et al. | |
| 5,218,969 A * | 6/1993 | Bredesen et al. | 600/523 |
| 5,239,997 A | 8/1993 | Guarino et al. | |
| 5,259,373 A | 11/1993 | Gruenke et al. | |
| 5,309,922 A | 5/1994 | Schechter et al. | |
| 5,311,875 A | 5/1994 | Stasz | |
| 5,316,002 A | 5/1994 | Jackson et al. | |
| 5,318,038 A | 6/1994 | Jackson et al. | |
| 5,331,967 A | 7/1994 | Akerson | |
| 5,361,767 A | 11/1994 | Yukov | |
| 5,417,215 A | 5/1995 | Evans et al. | |
| 5,485,841 A | 1/1996 | Watkin et al. | |
| 5,492,129 A | 2/1996 | Greenberger | |
| 5,549,106 A | 8/1996 | Gruenke et al. | |
| 5,553,609 A | 9/1996 | Chen et al. | |
| 5,560,351 A | 10/1996 | Gravenstein et al. | |
| 5,562,608 A | 10/1996 | Sekins et al. | |
| 5,588,439 A | 12/1996 | Hollub | |
| 5,591,130 A | 1/1997 | Denton | |
| 5,620,004 A | 4/1997 | Johansen | |
| 5,666,960 A | 9/1997 | Fredberg et al. | |
| 5,671,733 A | 9/1997 | Raviv et al. | |
| 5,746,699 A | 5/1998 | Fredberg et al. | |
| 5,769,084 A | 6/1998 | Katz et al. | |
| 5,782,240 A | 7/1998 | Raviv et al. | |
| 5,797,852 A | 8/1998 | Karakasoglu et al. | |
| 5,836,891 A | 11/1998 | DiMarogonas | |
| 5,844,997 A * | 12/1998 | Murphy, Jr. | 381/92 |
| 5,882,314 A | 3/1999 | Fredberg et al. | |
| 5,884,997 A | 3/1999 | Stanuch et al. | |
| 5,893,361 A * | 4/1999 | Hughes | 128/200.24 |
| 5,919,139 A | 7/1999 | Lin | |
| 5,919,144 A | 7/1999 | Bridger et al. | |
| 6,045,514 A | 4/2000 | Raviv et al. | |
| 6,058,932 A * | 5/2000 | Hughes | 128/200.24 |
| 6,062,216 A | 5/2000 | Corn | |
| 6,116,241 A * | 9/2000 | Huygen et al. | 128/204.23 |
| 6,139,505 A * | 10/2000 | Murphy | 600/532 |
| 6,142,952 A | 11/2000 | Behbehani et al. | |
| 6,164,277 A | 12/2000 | Merideth | |
| 6,168,568 B1 * | 1/2001 | Gavriely | 600/529 |
| 6,202,646 B1 | 3/2001 | Camodeca et al. | |
| 6,213,955 B1 | 4/2001 | Karakasoglu et al. | |
| 6,241,683 B1 | 6/2001 | Macklem et al. | |
| 6,261,238 B1 * | 7/2001 | Gavriely | 600/532 |
| 6,279,677 B1 | 8/2001 | Sanchez-Zambrano | |
| 6,287,264 B1 | 9/2001 | Hoffman | |
| 6,364,849 B1 | 4/2002 | Wilcox | |
| 6,375,623 B1 | 4/2002 | Gavriely | |
| 6,381,559 B1 | 4/2002 | Huang | |
| 6,383,142 B1 | 5/2002 | Gavriely | |
| 6,394,967 B1 | 5/2002 | Murphy | |
| 6,428,483 B1 | 8/2002 | Carlebach | |
| 6,432,057 B1 | 8/2002 | Mazess et al. | |
| 6,440,083 B1 | 8/2002 | Fredberg et al. | |
| 6,443,907 B1 | 9/2002 | Mansy et al. | |
| 6,454,724 B1 | 9/2002 | Greene | |
| 6,491,641 B1 | 12/2002 | Rasmussen | |
| 6,517,497 B2 | 2/2003 | Rymut et al. | |
| 6,580,944 B1 | 6/2003 | Katz et al. | |
| 6,595,928 B2 | 7/2003 | Mansy et al. | |
| 6,738,734 B1 | 5/2004 | Huang | |
| 6,790,183 B2 * | 9/2004 | Murphy | 600/532 |
| 6,811,538 B2 | 11/2004 | Westbrook et al. | |
| 6,942,626 B2 | 9/2005 | Salisbury et al. | |
| 7,127,290 B2 | 10/2006 | Girouard et al. | |
| 7,347,824 B2 | 3/2008 | Wilkinson et al. | |
| 7,479,115 B2 * | 1/2009 | Savic | 600/529 |
| 7,520,861 B2 * | 4/2009 | Murphy | 600/529 |
| 7,559,903 B2 * | 7/2009 | Moussavi et al. | 600/538 |
| 7,708,697 B2 | 5/2010 | Wilkinson et al. | |
| 7,819,814 B2 | 10/2010 | Gavriely et al. | |
| 7,850,618 B2 | 12/2010 | Wilkinson | |
| 2002/0002327 A1 | 1/2002 | Grant et al. | |
| 2002/0014235 A1 | 2/2002 | Rogers et al. | |
| 2002/0072685 A1 | 6/2002 | Rymut et al. | |
| 2002/0183642 A1 | 12/2002 | Murphy | |
| 2002/0193697 A1 | 12/2002 | Cho et al. | |
| 2003/0033094 A1 | 2/2003 | Huang | |
| 2003/0034035 A1 | 2/2003 | Raphael | |
| 2003/0045806 A1 | 3/2003 | Brydon | |
| 2003/0069502 A1 | 4/2003 | Makin et al. | |
| 2003/0120182 A1 | 6/2003 | Wilkinson et al. | |
| 2004/0010202 A1 | 1/2004 | Nakatani et al. | |
| 2004/0059240 A1 | 3/2004 | Cho et al. | |
| 2004/0069304 A1 | 4/2004 | Jam | |
| 2004/0236241 A1 * | 11/2004 | Murphy | 600/529 |
| 2004/0254493 A1 | 12/2004 | Chervin et al. | |
| 2005/0005935 A1 | 1/2005 | Gradon | |
| 2005/0011279 A1 | 1/2005 | Takeda et al. | |
| 2005/0020932 A1 | 1/2005 | Haberland et al. | |
| 2005/0027207 A1 | 2/2005 | Westbrook et al. | |
| 2005/0043645 A1 | 2/2005 | Ono et al. | |
| 2005/0096557 A1 | 5/2005 | Vosburgh et al. | |
| 2005/0154307 A1 | 7/2005 | Hirayama et al. | |
| 2005/0187464 A1 | 8/2005 | Ho et al. | |
| 2006/0243280 A1 | 11/2006 | Caro | |
| 2007/0055175 A1 | 3/2007 | Caro | |
| 2007/0118054 A1 | 5/2007 | Pinhas et al. | |
| 2008/0177195 A1 | 7/2008 | Armitstead | |
| 2008/0283062 A1 | 11/2008 | Esposito | |
| 2009/0203972 A1 | 8/2009 | Heneghan et al. | |
| 2009/0216127 A1 | 8/2009 | Gavriely | |
| 2010/0274554 A1 | 10/2010 | Orr et al. | |
| 2011/0230777 A1 * | 9/2011 | Fu | 600/529 |
| 2012/0215126 A1 | 8/2012 | Gavriely | |
| 2012/0302921 A1 | 11/2012 | Gavriely | |

FOREIGN PATENT DOCUMENTS

| | | |
|---|---|---|
| FR | 2299633 | 8/1976 |
| FR | 672793 A1 | 2/1991 |
| FR | 2672793 | 8/1992 |
| GB | 2240392 | 7/1991 |
| JP | 2005-066044 | 3/2005 |
| RU | 2177759 C1 | 1/2001 |
| WO | WO-88/02237 | 4/1988 |
| WO | WO91/03981 | 4/1991 |
| WO | WO96/19142 | 6/1996 |
| WO | WO97/00643 | 1/1997 |
| WO | WO-97/29687 | 8/1997 |
| WO | WO97/29687 | 8/1997 |
| WO | WO-98/14116 | 4/1998 |
| WO | WO98/14116 A2 | 4/1998 |
| WO | WO98/14116 A3 | 4/1998 |
| WO | WO-99/32035 | 7/1999 |
| WO | WO-99/52437 | 10/1999 |
| WO | WO-00/27282 | 5/2000 |
| WO | WO00/22735 A1 | 6/2000 |
| WO | WO-00/33735 | 6/2000 |
| WO | WO00/44281 | 8/2000 |
| WO | WO-01/80741 | 11/2001 |
| WO | WO01/80742 A1 | 11/2001 |
| WO | WO-02/13677 | 2/2002 |
| WO | WO02/13677 A2 | 2/2002 |
| WO | WO02/13677 A3 | 2/2002 |
| WO | WO-02/13697 | 2/2002 |
| WO | WO-02/30280 | 4/2002 |
| WO | WO-02/43579 | 6/2002 |
| WO | WO02/43579 A2 | 6/2002 |
| WO | WO02/43579 A3 | 6/2002 |
| WO | WO-02/065901 | 8/2002 |
| WO | WO02/065901 A2 | 8/2002 |

| | | |
|---|---|---|
| WO | WO02/065901 A3 | 8/2002 |
| WO | WO-03/024335 | 3/2003 |
| WO | WO-03/061471 | 7/2003 |
| WO | WO-03/063701 | 8/2003 |
| WO | WO-03/071952 | 9/2003 |
| WO | WO-03/075739 | 9/2003 |
| WO | WO-03/092493 | 11/2003 |
| WO | WO03/092493 A3 | 11/2003 |
| WO | WO2004/091503 A2 | 10/2004 |
| WO | WO2004/091503 A3 | 10/2004 |
| WO | WO2013021383 A1 | 2/2013 |

OTHER PUBLICATIONS

Murphy, R. et al. "Inhomogeneity of the Timing of Lung Sounds in Patients with Chronic Obstructive Lung Disease", Faulkner Hospital, Boston, MA.

Murphy, R. et al. "Spectral Characteristics of Lung Sounds in Patients with Chronic Obstructive Lung Disease," Faulkner Hospital, Boston, MA.

Poort, K.L., et al., "Airway Area by Acoustic Reflection: A Corrected Derivation for the Two-Microphone Method,", Journal of Biomechanical Engeering (Dec. 1999) vol. 121, pp. 663-665.

Louis, B., et al., "Airway Area by Acoustic Reflection: The Two-Microphone Method,", Journal of Biomechanical Engineering, (Aug. 1993) vol. 115, pp. 278-285.

Marshall, I., et al., "Acoustic Reflectometry for Airway Measurements in Man: Implementation and Validation,", Physiol. Meas. 14 (1993) 157-169, (Printed in the UK).

Rubinstein, I., et al., "Effect of mouthpiece, noseclips, and head, position on airway area measured by acoustic reflectons," The American Physiological Society, (1987) pp. 1469-1474.

Brooks, Lee J., et al., "Reproductivity and accuracy of airway area by acoustic reflection," Journal of Applied Physiology, (1986) pp. 777-787.

Fredberg, Jeffrey J., "Airway area by acoustic reflections measured at the mouth," Journal of Applied Physiology (1980) pp. 749-758.

Sidell, R.S., et al., "Noninvasive Inference of Airway Network Geometry From Broadband Lung Reflection Data," Journal of Biomechanical Engineering, (Aug. 1978), vol. 100, pp. 131-138.

Jackson, Andrew C., et al. "Airway geometry by analysis of acoustic pulse response measurements," Journal of Applied Physiology, (1977), pp. 523-536.

Ware, Jerry A., et al., "Continuous and Discrete Inverse-Scattering Problems in a Stratified Elastic Medium, I. Plane Waves at Normal Incidence," The Journal of the Acoustical Society of America, (1969), pp. 911-921.

Faber, C.E., et al., "Flextube reflectometry for localization of upper airway narrowing—a preliminary study in models and awake subjects," Respiratory Medicine (2001) vol. 95, pp. 631-638.

Carrive, Jean, et al., "Biophony: An Open System to Measure the Airway Area by Acoustic Reflection," IEEE Eng. in Medicine and Biology Society (1996), pp. 125-126.

Huang, J et al. "A new nasal acoustic reflection technique to estimate pharyngeal cross-sectional area during sleep" Journal of Applied Physiology (2000) vol. 88, pp. 1457-1466.

Dalmay, F et al. "*Acoustic properties of the normal chest*" Eur.Respir. J. (1995) vol. 8, pp. 1761-1769.

Gavriely, N. et al. "*Airflow effects on amplitude and spectral content of normal breath sounds*" American Physiology Society (1996) vol. 80(1) pp. 5-13.

Rasanen, J et al. "Detection of porcine oleic acid-induced acute lung injury using pulmonary acoustics" Journal of Applied Physiology (2002) vol. 93, pp. 51-57.

Pohlmann, A et al. "Effect of changes in lung volume on acoustic transmission through the human respiratory system" Physiol. Meas. (2001) vol. 22 pp. 233-243.

Mahagnah, M et al. "*Gas density does not affect pulmonary acoustic transmission in normal men*" American Physiology Society (1995) vol. 78(3) pp. 928-937.

Wodicka, G et al. "*Phase Delay of Pulmonary Acoustic Transmission from Trachea to Chest Wall*" IEEE Transactions on Biomedical Engineering (1992) vol. 39, No. 10, pp. 1053-1059.

Karnath, B et al. "*Pulmonary Auscultation*" Hospital Physician (2002) pp. 22-26.

Pasterkamp, H et al. "*Respiratory Sounds advances beyond the stethoscope*" Am. J. Respir. Crit. Care Med. (1997) vol. 156 pp. 974-987.

Räsänen, J et al. "Response of acoustic transmission to positive airway pressure therapy in experimental lung injury" Intensive Care Med (2005) vol. 31 pp. 1434-1441.

Carroll, P "Screening Spirometry: Dispelling Myths to Optimize Use" RT Magazine (2005) pp. 1-4.

Murphy, R et al. "Sound Speed in the Lung Measured by Sound Injection into Supraclavicular Space" —Poster, publication details unknown.

Leung, A et al. "Sound transmission between 50 and 600 Hz in excised pig lungs filled with air and helium" Journal of Applied Physiology (2000) vol. 89, No. 6, pp. 2472-2482.

Bergstresser, T et al. "*Sound transmission in the lung as a function of lung volume*" Journal of Applied Physiology (2002) vol. 93, No. 2, pp. 667-674.

Leung, AH et al. "*Sound transmission through normal and diseased human lungs*" Engineering Science and Education Journal (1996) pp. 25-31.

Wodicka, G et al. "*Spectral Characteristics of Sound Transmission in the Human Respiratory System*" IEEE Transactions on Biomedical Engineering (1990) vol. 37, No. 12 pp. 1130-1135.

Kraman, SS "*Speed of low-frequency sound through lungs of normal men*" Journal of Applied Physiology (1983) vol. 55 No. 6 pp. 1862-1867.

Kraman, SS et al. "*Transmission to the chest of sound introduced at the mouth*" Journal of Applied Physiology (1989) vol. 66 No. 1 pp. 278-281.

Paciej, R et al. "*Transpulmonary speed of sound input into the supraclavicular space*" Journal of Applied Physiology (2003) vol. 94 pp. 604-611.

Berger, PJ et al. "*Velocity and attenuation of sound in the isolated fetal lung as it is expanded with air*" Journal of Applied Physiology (2005) vol. 98 pp. 2235-2241.

Pedersen, PC et al. "*Ultrasound properties of lung tissue and their measurements*" Ultrasound in Med. & Biol. (1986) vol. 12, No. 6, pp. 483-499.

Dunn, F "Attenuation and speed of ultrasound in lung: Dependence upon frequency and inflation" J. Acoust. Soc. Am. 80(4) (1986) pp. 1248-1250.

Pohlmann, A et al. "*Can human acoustic respiratory impedance form the basis for lung imaging?*" Medical & Biological Engineering & Computing (1999) vol. 37, Supp. 2, Pt II, pp. 952-953.

Goncharoff, V et al. "*Wideband acoustic transmission of human lungs*" Medical & Biological Engineering & Computing (1989) vol. 27, No. 5, pp. 513-519.

Supplemental Partial European Search Report for EP01925200 dated Nov. 27, 2008.

Non-Final Office Action for U.S. Appl. No. 10/272,494 dated May 15, 2007.

Non-Final Office Action for U.S. Appl. No. 11/111,689 dated Sep. 24, 2007.

Non-Final Office Action for U.S. Appl. No. 11/124,326 dated Aug. 22, 2008.

Interview Summary for U.S. Appl. No. 11/124,326 dated Jul. 18, 2008.

Advisory Action for U.S. Appl. No. 11/124,326 dated Jul. 18, 2008.

Final Office Action for U.S. Appl. No. 11/124,326 dated Mar. 3, 2008.

Non-Final Office Action for U.S. Appl. No. 11/124,326 dated Sep. 14, 2007.

Advisory Action for U.S. Appl. No. 11/116,667 dated Oct. 15, 2008.

Interview Summary for U.S. Appl. No. 11/116,667 dated Sep. 26, 2008.

Final Office Action for U.S. Appl. No. 11/116,667 dated Jun. 26, 2008.

Non-Final Office Action for U.S. Appl. No. 11/116,667 dated Aug. 21, 2007.

Non-Final Office Action for U.S. Appl. No. 11/107,999 dated Jan. 28, 2009.

Non-Final Office Action for U.S. Appl. No. 11/107,999 dated Dec. 7, 2007.
T. Rosqvist, et al. "Tool Kit for Lung Sound Analysis" Medical and Biological Engineering & Computing, vol. 33, No. 2 Mar. 1995, pp. 190-195.
A. Cohen, et al.: "Analysis and Automatic Classification of Breath Sounds" IEEE Transactions on Biolmedical Engineering, vol. 31, No. 9, Sep. 1984, NY, USA pp. 585-590.
Pseudo-noise (PN). (2001). In Hargrave's Communications Dictionary, Wiley. Retrieved Dec. 5, 2007, from http://www.credoreference.com/entry/2723988.
"Pseudorandom noise" from Wikipedia, the free encyclopedia. Retrieved Dec. 5, 2007 from http://en.wikipedia.org/wiki/Pseudo-random.sub.--noise.
Huang et al. "Use of Intrinsic Modes in Biology: Examples of indicial response of pulmonary blood pressure to +- step hypoxia", Proc. Natl. Acad. Sci. USA vol. 95, pp. 12766-12771, Oct. 1998.
Huang et al. "Engineering analysis of biological variables: An example of blood pressure over 1 day", Proc. Natl. Acad. Sci. USA vol. 95, pp. 4816-4821, Apr. 1998.
Huang, Norden E. et al, The Empirical Mode Decomposition and the Hilbert Spectrum for Nonlinear and Non-Stationary Time Series Analysis, Proc. Roy Soc. London, pp. 903-955, .COPYRGT. 1998.
Huang, Norden E. et al, (Abstract)—A New View of Nonlinear Waves; The Hilbert Spectrum, Annual Review of Fluid Mechanics, Jan. 1999.
Katz Richard A., Chaotic Circuits for Communication, International Society for Optical Engineering, vol. 2612, Oct. 1995.
Ono, M. et al.; "Separation of Fine Crackles from Vesicular Sounds by a Nonlinear Digital Filter"; IEEE Transactions on Biomedical Engineering; vol. 36; No. 2; pp. 286-291; Feb. 1989; XP 000186148.
Wodicka et al.; "Bilateral Asymmetry of Respiratory Acoustic Transmission;" Sep. 1994; Medical & Biological Engineering & Computing; vol. 32, pp. 489-494; XP000469338.
Jingping, X. et al; "Spectrum Analysis of Lung Sounds"; Images of the Twenty First Century; vol. part 5; No. conf. 11; pp. 1676-1677; Nov. 9, 1989.
Goncharoff, V., et al. "Wideband Acoustic Transmission of Human Lungs" Meidcal and Biological Enginieering & Comoputing (1989) vol. 27, No. 5, pp. 513-519.
Karnath, M.D. "Pulmonary Auscultation," Hospital Physician, Jan. 2002, pp. 22-26.
Basano, L. et al; "A DSP Breath Sound Analyser"; Proceedings of the International Symposium on Circuits and Systems, ESPOO; vol. 3; No. conf. 21; pp. 2631-2634; Jun. 7, 1988.

* cited by examiner

| Respiratory Sound | Mechanisms | Origin | Acoustics | Relevance |
|---|---|---|---|---|
| Basic Sounds | | | | |
| Normal lung sound | Turbulent flow vortices, unknown mechanisms | Central airways (expiration), lobar to segmental airway (inspiration) | Low-pass filtered noise (range < 100 to > 1,000 Hz) | Regional ventilation, airway caliber |
| Normal tracheal sound | Turbulent flow, flow impinging on airway walls | Pharynx, larynx, trachea, large airways | Noise with resonances (range < 100 to > 3,000 Hz) | Upper airway configuration |
| Adventitious Sounds | | | | |
| Wheeze | Airway wall flutter, vortex shedding | Central and lower airways | Sinusoid (range ~ 100 to > 1,000 Hz; duration, typically > 80 ms) | Airway obstruction, flow limitation |
| Rhonchus | Rupture of fluid films, airway wall vibrations | Larger airways | Series of rapidly dampened sinusoids (typically < 300 Hz and duration > 100 ms) | Secretions, abnormal airway collapsibility |
| Crackle | Airway wall stress - relaxation | Central and lower airways | Rapidly dampened wave deflection (duration typically < 20 ms) | Airway closure, secretions |

*FIG. 4*

METHOD OF DETERMINING LUNG CONDITION INDICATORS

CROSS REFERENCE TO RELATED APPLICATIONS

The present application is a Continuation-in-Part application of U.S. application Ser. No. 11/116,667 filed Apr. 27, 2005, now abandoned.

The present application is related to U.S. application Ser. No. 11/107,999 filed Apr. 15, 2005 by Wilkinson et al., entitled "Method And Apparatus For Determining Conditions Of Biological Tissues", which published as US 2006-0037615 on Feb. 23, 2006, now U.S. Pat. No. 7,708,697 issued May 4, 2010, and U.S. application Ser. No. 10/272,494 filed Oct. 15, 2002 by Wilkinson et al., entitled "Method and Apparatus for Determining Conditions of Biological Tissues," which published as US 2003-0120182 A1 on Jun. 26, 2003, now U.S. Pat. No. 7,347,824, which is a continuation of Patent Cooperation Treaty Application No. PCT/AU01/00465, filed on Apr. 20, 2001, and published as WO 2001/080741 on Nov. 1, 2001, which claims priority to Australian Provisional Application Nos. AU PQ7040 and AU PR4333, filed on Apr. 20, 2000 and Apr. 10, 2001, respectively. The present application is also related to U.S. application Ser. No. 11/111,689 filed on Apr. 21, 2005 by Wilkinson et al., entitled "Apparatus and Method for Lung Analysis," which published as US 2006-01000666 A1 on May 11, 2006, and is now abandoned, and which was a continuation-in-part of aforementioned U.S. application Ser. No. 10/272,494. The present application is also related to Australian Application Nos. AU 2001252025 and 2004222800, filed on Apr. 20, 2001 and Oct. 4, 2004, respectively, and now ceased. Each of the foregoing applications, provisional applications, and publications, is hereby incorporated herein, in its entirety, by this reference.

FIELD OF THE INVENTION

The present invention relates to a method and apparatus for determining characteristics of biological tissues in humans and animals. In particular, it relates to determining the characteristics of tissues such as the lungs and airways.

BACKGROUND OF THE INVENTION

Non-invasive determination of the condition of the pulmonary system is useful in determining proper medical treatment.

Ultrasonic waves have been used to monitor and observe the condition of patients and of selected tissues. However, ultrasonic techniques are not very effective in tissues in which there is a substantial quantity of gas, such as the lung.

Respiratory problems ail infants and adults alike. Among infants, respiratory failure is a common problem requiring support and is usually treated with a period of mechanical ventilation. Over the last decade the mortality of infants suffering respiratory failure has shown an impressive decline and the vast majority of infants now survive initial acute respiratory illness, but lung injury associated with mechanical ventilation causes many infants to develop 'chronic lung disease.'Chronic lung disease is characterised by persisting inflammatory and fibrotic changes. Adults are often afflicted with different respiratory diseases or conditions. Some common lung diseases or conditions include emphysema, asthma, regional collapse (atelectasis), interstitial oedema and both focal lung disease (e.g. tumour) and global lung disease (e.g. emphysema).

A need exists for a simple, non-invasive and convenient system to monitor and assess the condition of the lung.

SUMMARY OF THE INVENTION

The present invention provides a non invasive method and apparatus for use in determination of lung condition.

One aspect of the invention provides a method of determining a condition of at least one lung of a patient. The method includes making an active measurement of the at least one lung by introducing a signal comprising one or more audible frequencies into the at least one lung and receiving the at least one audible frequency signal during or upon passage through the at least one lung, making a passive measurement of the at least one lung by receiving at least one naturally occurring sound associated with breathing by the patient, and determining a condition of the at least one lung by combining data associated with the active measurement with data associated with the passive measurement.

Another aspect of the invention provides a method of determining the condition of a patient's lung. The method includes injecting a signal comprising audible frequencies through the patient's lung, recording the injected signal and processing the signal to determine a first set of criteria indicative of a condition of the lung, monitoring naturally occurring breath sounds of the patient's lung, processing the breath sounds of the patient's lung to determine a second set of criteria indicative of a condition of the lung, and narrowing the number of criteria indicative of a condition of the lung by comparing the first set of criteria from the injected signal with the second set of criteria from the naturally occurring breath sounds.

Yet another aspect of the invention provides apparatus for evaluating the condition of a lung of a patient. The apparatus comprises one or more emitting transducers introducing a signal comprising audible frequencies into the lung, one or more receiving transducers that receive the introduced signal after it has passed through at least part of the lung, and a processing unit that monitors the received signal and determines a first set of indicators of a condition of the lung based on the received signal, and monitors one or more naturally occurring sounds associated with breathing by the patient and determines a second set of indicators of a condition of the lung based on the one or more monitored naturally occurring sounds, and compares the first and second set of indicators, and provides a third set of indicators corresponding to a portion of overlap of the first and second sets of indicators respectively, the third set of indicators being indicators of lung condition based upon both the introduced signal and the naturally occurring sounds.

Another aspect of the invention provides apparatus for evaluating the condition of a lung. The apparatus includes an emitting transducer that injects a signal having audible frequencies through the lung, one or more receiving transducers that receive the injected signal, the one or more receiving transducers also monitoring natural breath sounds of the lung and means for producing an indication of the condition of the lung based upon both the natural breath sounds and upon the received injected signal.

Another aspect of the invention still, provides a method of determining the condition of a patient's lung which includes injecting a signal having audible frequencies into the patient's lung, determining the speed of sound of the injected audible signal through the lung tissue, calculating a property of the lung tissue and correlating the property with a first indication of the condition of the patient's lung. The method also includes monitoring an amplitude of a breath sound of the patient's lung as the patient inhales and exhales, correlating the monitored breath sound amplitude with a second indication of the condition of the patient's lung and combining the first and second indications to narrow the possibilities of the condition of the patient's lung.

BRIEF DESCRIPTION OF THE DRAWINGS

The present invention will now be described in greater detail with reference to the accompanying drawings. It is to be understood that the particularity of the accompanying drawings does not supersede the generality of the preceding description of the invention.

A reference numeral, letter, and/or symbol that is used in one drawing to refer to a particular element or feature may be used in another drawing to refer to a like element or feature.

FIG. 4 is a chart of normal and adventitious respiratory sounds.

DETAILED DESCRIPTION

Figure 1:
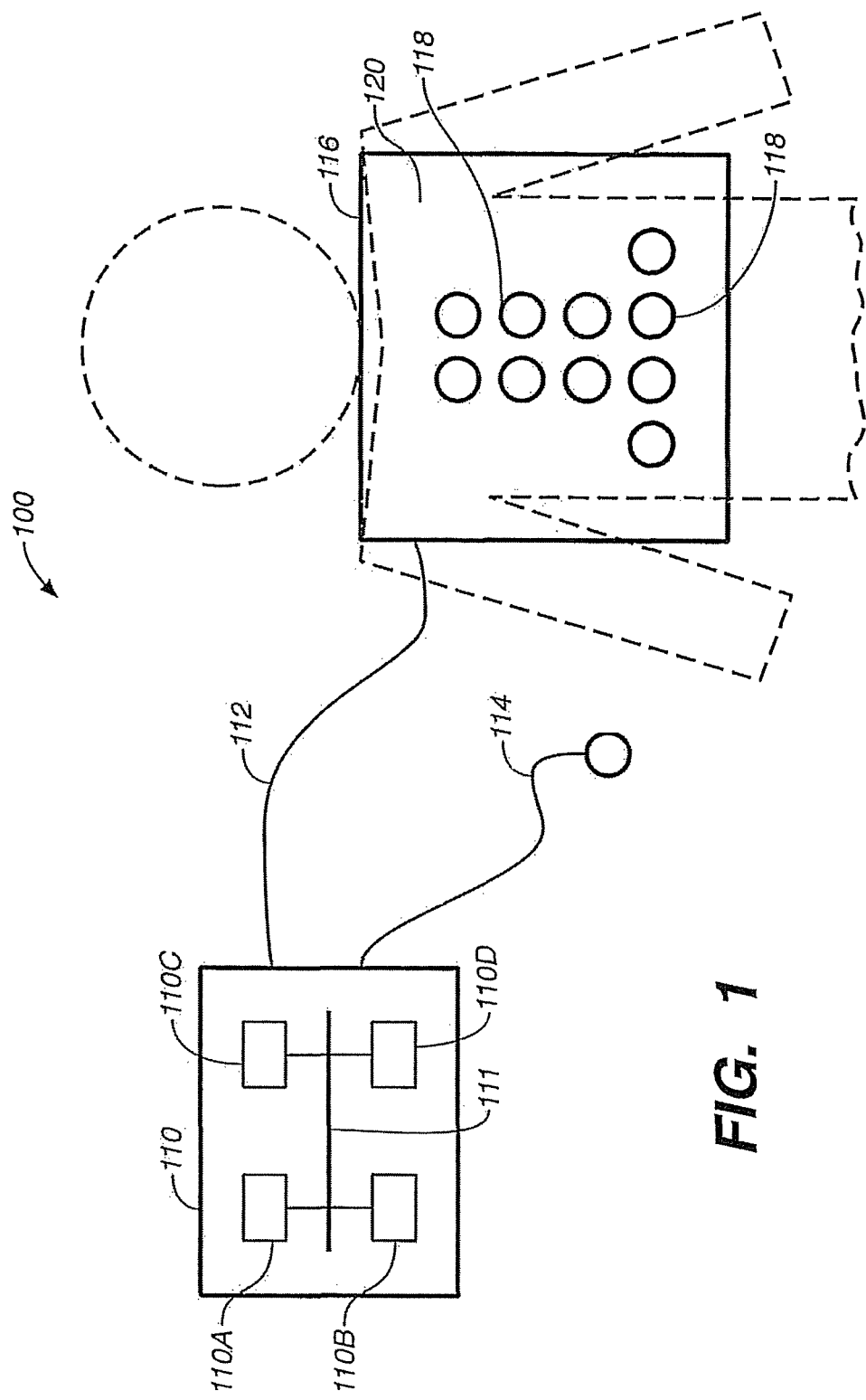
FIG. 1 is schematic illustration of system 100.

The present invention utilizes a combination of two different techniques to aid in determination of the condition of the lungs. The first technique is passive auscultation, which involves listening to the natural breath sounds of the lungs as a patient inhales and exhales (during inspiration and expiration). Passive auscultation goes back to the early 1800's when the stethoscope and associated techniques were developed. Of course, modern electronics provide for much more sophisticated measurement and analysis. The second technique is active auscultation which involves actively introducing a sound signal in the lungs and monitoring the signal after it passes through some portion of the lungs. Unlike ultrasonic techniques, this utilizes a lower frequency spectrum comprising audible frequencies.

An understanding of the theoretical aspects of sound transmission in tissue is helpful for the best use of bio-acoustic data which is obtained using the present invention.

The term "auscultation" is commonly used and well known in medical circles. Herein, the concept or technique commonly known simply as "auscultation" is referred to as "passive auscultation" in order to distinguish it from an "active auscultation" concept or technique associated with the present invention, as further described below.

Active Auscultation

The term "active auscultation" generally refers to actively introducing at least one audible frequency signal into the body or a portion thereof and thereafter receiving and/or monitoring the signal after it has passed through some portion of the body. This is done to aid in the diagnosis and/or treatment of the body or a portion thereof. The audible signal that is introduced to the body or portion thereof may be selected to suit its particular application, and signal parameters can be tailored to the application. Examples of the parameters include but are not limited to: the time of the introduction of the sound or any of various parameters of the sound, such as the sound pressure level, the phase of the sound, the frequency of the sound, the velocity of the sound, and the like, for example, such that the relative nature or condition of the second derivative or responsive sound may be analyzed in a meaningful way, such as quantitatively, for example.

In general, active auscultation may involve the cross-correlation of the introduced signal as it is introduced to the body or a portion thereof and the signal as it is received after passing through some portion of the body, be it transmitted, reflected, scattered, refracted, and/or the like, and obtaining meaningful information from the correlation, such as a time delay or a phase shift, etc. The information obtained may concern a single parameter, such as a sound velocity, for example, multiple parameters, such as a sound velocity and a sound attenuation, for example, and/or a ratio of parameters, such as a ratio of a first sound velocity and a second sound velocity, for example, as further described herein.

According to embodiments of the present invention, any of various parameters of the received signal may be determined. A consideration of a single parameter may be useful in assessing or determining a condition of a body or a portion of a body. Examples of such single parameters include an amplitude, a pressure, a velocity, a frequency, an attenuation, a phase, a time, and the like, associated with the injected and/or received signal. As will be discussed later, consideration of multiple parameters can be of even greater utility.

A unique feature of audible signal propagation through the lung parenchyma is that the velocity is less than that expected for either tissue (1500 ms$^{-1}$) or air (343 ms$^{-1}$). This can be explained, in part, by examining the basic relationship between audible signal velocity v and the physical properties of the lung tissue through which the audible signal is propagating. This relationship is:

$$v = \frac{1}{\sqrt{\rho C}}, \tag{1}$$

where $\rho$ is the density and C is the volumetric compliance or inverse volumetric stiffness per unit volume. In determining the velocity of an audible signal in air, substituting an air density of 1.2 kgm$^{-3}$ and an air compliance of 7.14×10$^{-6}$ Pa$^{-1}$ yields an audible signal velocity in air of 342 ms$^{-1}$.

It has been shown that this relationship also holds for composite porous materials with a closed cell structure which is similar to that of the lung, but where $\rho$ and C are replaced by the tissue's average or composite values. For more information please refer to Rice, D. A. (1983) Sound speed in pulmonary parenchyma. J. Appl. Physiol. 54:304-308, which is hereby incorporated by this reference in its entirety. Expressing these values in terms of the volumetric fraction of tissue h and of gas (1−h) and the constituent densities and compliances gives tissue density:

$$\rho = (1-h)\rho_g + h\rho_t \tag{2},$$

and volumetric compliance:

$$C = (1-h)C_g + hC_t \tag{3},$$

where $\rho$, $\rho_g$, $\rho_t$ are the composite, gas and tissue densities respectively and C, $C_g$, $C_t$ are the composite, gas and tissue volumetric compliances respectively.

Substituting equations (2) and (3) into equation (1) yields an expression which relates audible signal velocity through a composite structure to the volumetric fraction and the physical properties of both the tissue and gas which compose the material:

$$v = \frac{1}{\sqrt{((1-h)\rho_g + h\rho_t)((1-h)C_g + hC_t)}}. \quad (4)$$

It must also be noted that the density of air is approximately 3 orders of magnitude less than that of most tissues and the volumetric compliance of air is some 4 orders of magnitude larger than that of most tissues. This can be used to determine the velocity of audible signal propagation through the lung for a range of volumetric fractions which are likely to be seen in the lung, (0.05 at TLC to 0.5 to 0.9 for a fully atelectatic/collapsed lung). These velocities can be determined by simplifying equation 4 as follows:

$$v = \frac{1}{\sqrt{h(1-h)}} \frac{1}{\sqrt{\rho_t C_g}}. \quad (5)$$

Equation 5 illustrates the dependence that audible signal velocity has on the volumetric fraction of tissue, the volumetric fraction of air, the tissue density and the gas compliance. The tissue compliance and the gas density play essentially no role in the determination of velocity.

Audible signal velocity in composite materials is determined in part by the product of the tissue density and the gas compliance. The result of this is that the lung parenchyma appears to act like homogeneous mass-loaded air as far as audible signal propagation is concerned, such that the velocity of audible signal propagation through the tissue is markedly slower than through air. Substitution of known values for tissue density, $\rho_t$ and gas compliance, $C_g$ in equation 5 gives:

$$v = \frac{11.82}{\sqrt{h(1-h)}}. \quad (6)$$

Differentiation of v in equation 6 with respect to h determines a minimum value for velocity at h=0.5 where v=23.6 ms$^{-1}$. For values of h<0.5 the velocity increases with decreasing lung density and conversely for h>0.5 the velocity decreases with decreasing lung density.

The quadratic properties of equation 6 result in the presence of two values for h for any particular value of measured velocity. These values are:

$$h = 0.5 \pm \sqrt{0.25 - 139.56/v^2} \quad (7).$$

Therefore, the determination as to whether h is above or below 0.5 must be made on physical grounds or by making paired velocity measurements where h is changed between measurements. The direction of the associated change in velocity (increasing or decreasing) can then be used to indicate whether h is above or below 0.5. Therefore, the volumetric fraction of tissue and gas in the lung and hence lung density can be determined directly from measuring the velocity of an audible signal as it propagates through the tissue. All of this theoretical explanation is given only to inform the reader on the underpinnings of auscultation and signal propagation. It should be understood that the present invention should not be limited in any way to use of these specific formulae and that calculations and processing techniques can be implemented in any number of ways.

The audible signal may be introduced in any non-invasive manner, such as by percussion, or using any mechanical, electrical or other transducer which is capable of generating acoustic sounds. It is preferable that the audible signal which is introduced to the tissue possesses properties which allow it to easily be distinguished from environmental noise which may be present. Examples may include a single tone or a sinusoidal wave. In a preferred embodiment of the invention, a pseudo-random noise is produced by an electro-acoustic transducer and introduced into the tissue. Looking at FIG. 1, the signal is produced by sending transducer 122 of measurement system 100. Sending transducer is placed in contact with the patient, preferably at some distance from signal receiver 116, such that the signal must pass through the lungs or other biological tissue that is being measured. Although one sending transducer is shown in FIG. 1, a plurality of sending transducers may alternatively be utilized. Signal receiver 116 has one or more receiving transducers 118. Preferably more than one transducer 118 is employed, and the transducers 118 can be arranged in any geometry. In the preferred embodiment shown, the transducers 118 are arranged in various locations within a support medium 120, which is preferably pliant or anatomically shaped and allows the transducers to maintain contact with the patient, either directly or though some thin sterile material.

The sending transducer(s) 122 and signal receiver 116 are respectively connected to control unit 110 through wires 114 and 112 respectively. Wireless transmission may alternatively be used in place of wires 114 and 112. Control unit 110 comprises processor 110A, display 110B, storage 110C, and human interface devices 110D. These are all connected by system bus 111 and other circuitry. Human interface devices may include a keyboard and mouse etc. . . . and display 110B may also be a touch screen type display. Various other circuitry (not shown) is included in control unit 110 for signal generation and processing. Control unit 110 may be a purpose built device or may be implemented within a personal computer with additional circuitry contained in a separate unit or insertable card.

It is preferable to use a pseudo-random noise signal that has characteristics which are similar to a white noise signal, but with mathematical properties which allow its amplitude to be defined at any moment in time. Introduction of the pseudo-random noise signal to the tissue may occur in bursts, preferably of 0.1 to 20 seconds duration, and the signals may be produced preferably with frequencies which range from 20 Hz to 25 kHz or 20 Hz to 50 kHz and at a sound pressure level of between 1 and 100 Pascal although these ranges are preferable only and are not to be taken as limiting the scope or application of the present invention.

The output of signal receiver 116 may be amplified using low noise isolation amplifiers and band-pass filtered with cut-off frequencies and roll-off characteristics which depend on the acoustic properties of the tissue which is being assessed. For example, for measurements made on the neonatal lung, the pass band is preferably between 50 Hz and 5 kHz with a roll-off which corresponds to that of a $4^{th}$ order linear phase filter. These filters remove any very low frequency environmental noise (e.g. below 10 Hz) that can adversely affect the performance of auto-scaling amplifiers into which the filtered signal may be fed.

The output signal from signal receiver 116 may be amplified by control unit 110 and is then processed. Processing may include a cross-correlation analysis of the input and output signals.

The cross-correlation function can be calculated using the output of any of sending transducers 122 as the input signal, x(t) and the output of any of the transducers 118 located on the other side of the tissue as the output signal, y(t) wherein the cross-correlation function can be calculated as:

$$R_{xy}(\tau) = \lim_{T \to \infty} \frac{1}{T} \int_0^T x(t) y(t+\tau) \, dt,$$

where T is the observation time, and $\tau$ is the delay time between x(t) and y(t) at which $R_{xy}(\tau)$ is calculated.

The impulse response of the system in the time domain can also be determined. It is preferable that the impulse response then undergoes Fast Fourier Transformation so that the signal is transformed into the frequency domain and the transfer function of the tissue can be determined. This transfer function provides a quantitative indication of the characteristics of the tissue, wherein:

(a) the magnitude of the transform provides data relating to the transmission of the audible signal as it propagates through the tissue as a function of frequency; and (b) the phase of the transform (after "unwrapping") can be used to calculate the phase difference, time delay and velocity of the audible signal for each frequency that is present in the psuedo-random noise signal which is introduced to the tissue by the acoustic transducer. Each of these may serve as an indicator of the condition of the lung.

A separate analysis of the relative transmission of the audible signal through the tissue can be used to identify resonant and anti-resonant frequencies of the tissue which is being assessed. Changes in these frequencies can then be used to assess regional differences in tissue topology which may be related to pathology. These are also examples of indicators of lung condition.

The cross-correlation function may be used to denote airway patency associated with the patient's respiratory system. Thus, the maximum value of the cross-correlation function $R_{xy}(\tau)$ may be denoted as "patency" as it is indicative of the transmission properties of the airways. A lower patency value may indicate constriction in the airways.

The Coherence function of the system can also be determined, using the output of any sending transducers 122 as the input signal x(t), and the output of any transducers 118 y(t), wherein the Coherence function $C_{xy}$ can be calculated as:

$$C_{xy} = \frac{|G_{xy}|^2}{G_{xx} G_{yy}}$$

where Gxy is the cross-spectral density between x and y, and Gxx and Gyy the autospectral density of x and y respectively. The magnitude of the Coherence function can be used to estimate the linear relationship between x and y.

The Coherence function can also be used to determine a threshold value influencing the selection of signal values or parameters which may be processed to make a determination of the condition of a lung. For example, coherence values greater than 0.7 may indicate a parameter is suitable for use in the calculation of other parameters e.g., the signal Transfer Function may be calculated only for frequency values that meet the threshold criteria (i.e. coherence greater than 0.7).

Despite numerous experimental investigations of transpulmonary audible signal transmission where the source of audible signal is placed at the mouth, there has been no theoretical model which described audible signal transmission through the thorax. The present invention may, but does not necessarily, employ a simple model based on the double wall transmission model that is used in architectural acoustics to describe the audible signal attenuating effect of double walls separated by a compliant air layer, as is present in the lung.

Figure 2A:
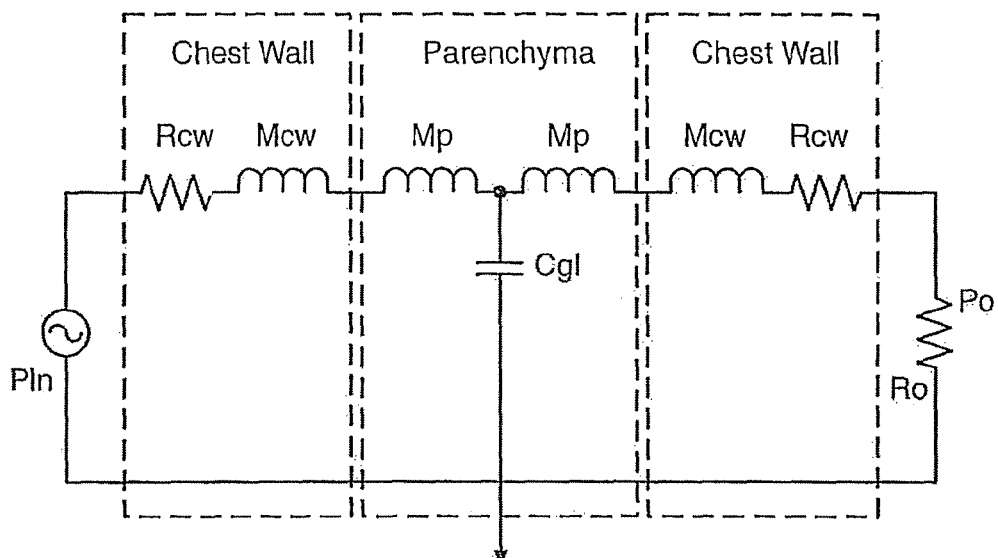
FIG. 2(a) illustrates an electric circuit modeling the acoustic characteristics of the thorax.

The main features of this model as it relates to the thorax can be represented by an electrical equivalent circuit that can be used to describe the pertinent features of audible signal transmission through the thorax. This model is illustrated in FIG. 2(a). This approach to the analysis of acoustic transmission across the thorax facilitates analysis using sophisticated circuit emulation software such as SPICE to explore the effect of changing model parameters. In the equivalent electric circuit model where:

$R_{cw}$ is the loss component associated with the chest wall and parenchyma;

$M_{cw}$, $M_p$ is the surface mass of the chest wall and parenchyma respectively;

$C_{gl}$ is the lung gas compliance;

$P_{in}$, $P_o$ are the acoustic input and output audible signal pressure levels respectively; and $R_0$ is the acoustic impedance of free space (414 MKS Rayls).

Figure 2B:
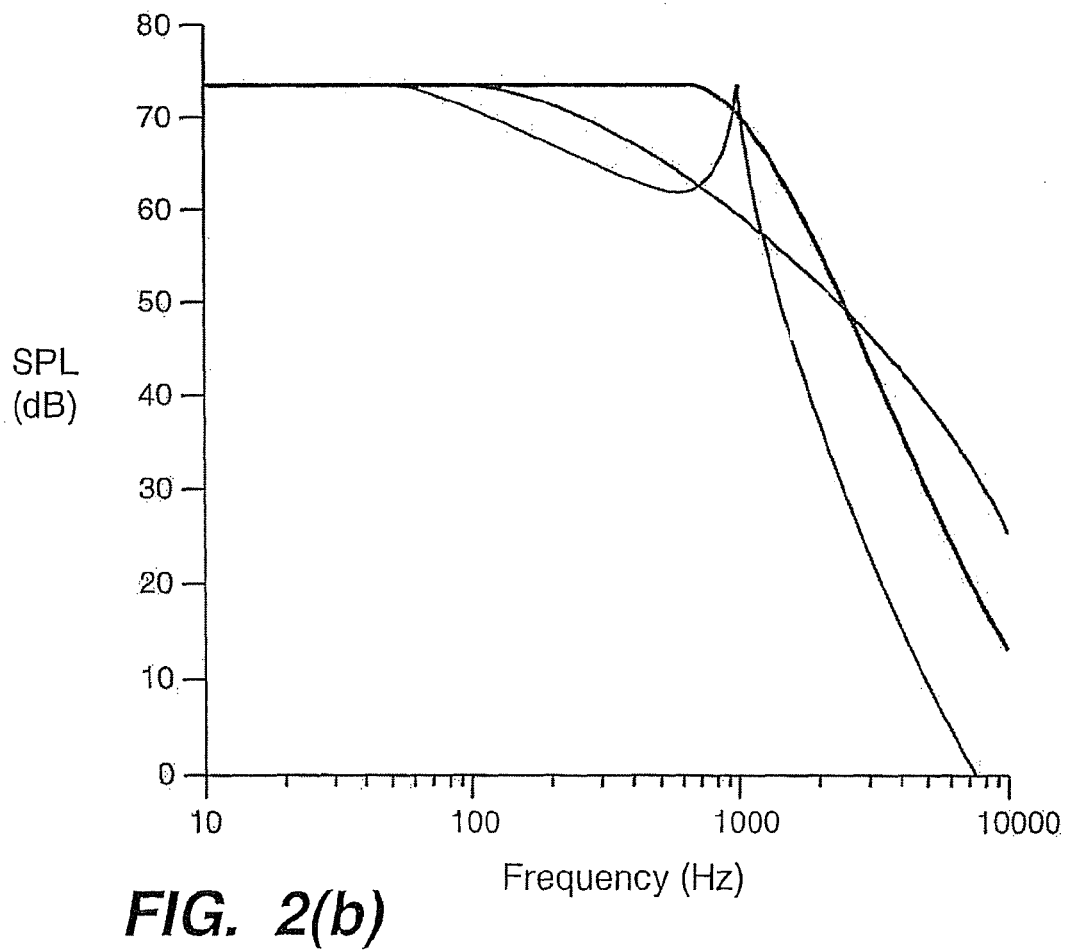
FIG. 2(b) illustrates (1) large, (2) moderate and (3) small acoustic losses as measured using the electric circuit model and which represents the output sound pressure level as would be measured at the chest.

As illustrated in FIG. 2(b), the model can be used to simulate the effect that changing $R_{cw}$ has on the transfer function of the equivalent circuit which represents the chest. This transfer function can be described mathematically as $P_o(f)/P_{in}(f)$ where f is the frequency and $P_{in}(f)$ and $P_o(f)$ are the input (transducer) and receiving transducer sound pressure levels (SPL) respectively. As $R_{cw}$ is decreased, the transfer function becomes progressively more peaked or resonant as illustrated by curves 1 to 3 in FIG. 2(b).

At sufficiently high frequencies, the output sound pressure level for all three curves falls asymptotically at a rate of 60 dB per decade. As the frequency is increased above the resonant frequency, the response is dominated by the inertial mass of the proximal and distal chest walls, and the shunt gas compliance of the lung. These act together to produce the 60 dB per decade fall-off, such that the thorax is, in effect, acting like a third order low-pass electrical filter. Analysis of the equivalent circuit, neglecting losses, shows that the resonant frequency of the thorax, $f_0$, can be determined using:

$$f_0 = \frac{1}{2\pi} \sqrt{\frac{2}{C_{gl}(M_{cw} + M_p)}}. \tag{8}$$

Furthermore, if the transfer function is measured at $f_0$ and at another frequency well above $f_0$, say, $3f_0$ then using an analysis of the equivalent circuit, an explicit expression for lung gas compliance, $C_{gl}$, can be deduced in the form $$C_{gl} = \frac{4.18 \times 10^{-2} G}{f_0}, \tag{9}$$

where $G=|P_o(f)/P_{in}(f)|$ and is the magnitude of the transfer function of the thorax measured at $3f_0$.

It follows that gas volume $V_{gl}$ can be computed using equation 10:

$$V_{gl} = \gamma P_0 C_{gl} \quad (10)$$

where γ is the adiabatic gas constant and $P_0$ is the atmospheric pressure.

An important component of acoustic transmission which can be modelled using the equivalent electric circuit is the loss component Rcw illustrated in FIG. 2(a) which includes acoustic loss in the chest wall and parenchyma. Because the chest wall is acoustically thin, the dissipative loss in the wall is negligible but the loss in the parenchyma, which includes a large number of serial mass-compliance interfaces formed from the tissue and gas comprising the parenchymal structure, may be considerable. One model that has been proposed to account for acoustic loss in the parenchyma comprises air bubbles in water, for which an analysis already exists. In this model, absorption occurs because acoustic work is required to alternately compress and expand these bubbles.

It has been shown that the plane wave attenuation produced by N bubbles over distance x is given by:

$$P(x) = P_0 e^{-\left(\frac{N\sigma}{2}\right)x}, \quad (11)$$

where $\sigma = 16\pi^2 r_o^4 \rho_t c_t R / \{R^2 + (\omega M - 1/\omega C)^2\}$;

P(x) is the SPL at x;
$P_o$ is the SPL at x=0;
$r_0$ bubble radius;
$c_t$ sound speed in tissue; and
R, M, C are the effective mechanical resistance, mass and compliance of the bubbles respectively.

Attenuation, $$\alpha = \frac{P(x)}{P_0}$$

in dB/cm can then be written as:

$$\alpha = 4.35 N\sigma \quad (12).$$

This is a complex function of R, M, C but a simplified expression for the attenuation can be deduced by recognizing that the acoustic vibration of the bubbles (alveoli) is dominated by bubble compliance C at frequencies which are much lower than resonance (i.e. <≈10 kHz for realistic alveoli sizes). Therefore, attenuation can be reduced to:

$$\alpha = 2.36 \times 10^{-2} r_0^6 f^3 N \quad (13).$$

The number of bubbles per unit volume N is approximately related to the gas fraction (1−h) by:

$$N = \frac{3(1-h)}{4\pi r_0^3}, \quad (14)$$

hence equation 13 can be written as $$\alpha = 1.35 \times 10^{-3} \frac{f^3 (1-h)^2}{N}. \quad (15)$$

From these equations, it can be seen that:

(a) absorption is related to the square of the gas fraction (1−h); a small increase in the tissue fraction h is associated with a marked decrease in high frequency attenuation. This may explain the increased transmission of audible signal across the chest wall which can be observed clinically at high frequencies, following pneumonic consolidation of the lung; and (b) attenuation is a strong function of both the frequency f and the alveolar radius $r_0$. This may explain, in part, the rapid fall-off in transmitted audible signal at high frequencies seen in both adult and neonatal subjects. The dependence on bubble radius may explain the reduced transmission through the thorax during emphysema.

Furthermore, these equations indicate that:

(a) absorption is related to the square of the gas fraction (1−h); and (b) audible signal transmission attenuation is a strong function of both the frequency and the alveolar radius.

Using these relationships between audible signal transmission velocity in tissues and the tissue characteristics themselves, it is possible to obtain a workable relationship between acoustic measurements and lung pathology or the pathology or condition of other biological tissues.

Figure 3A:
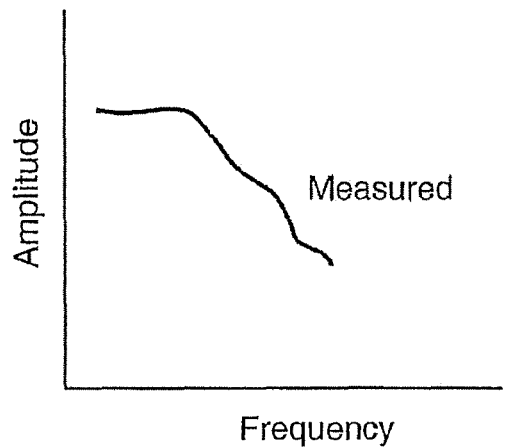
FIGS. 3A-3D are graphs of some measured and derived indicators associated with active auscultation.
Figure 3B:
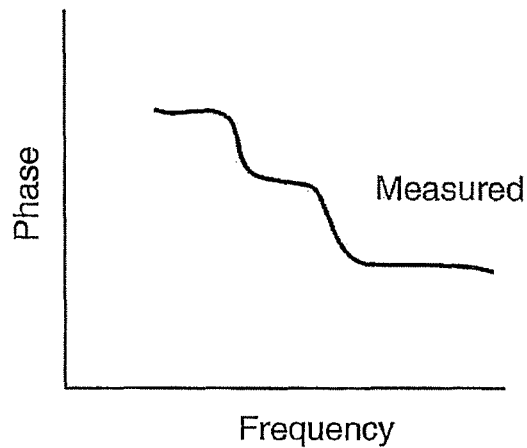
Figure 3C:
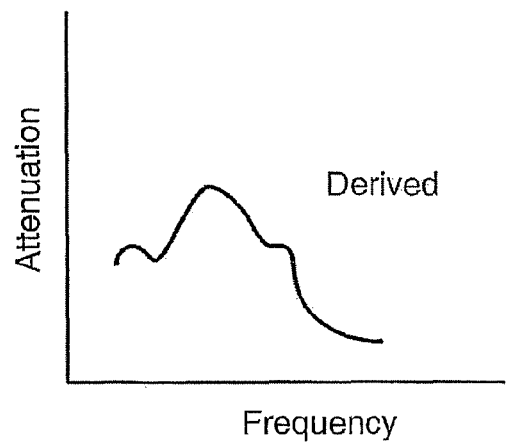
Figure 3D:
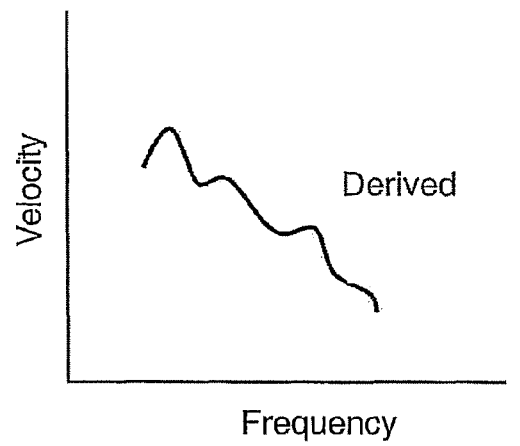

FIGS. 3A-3D are graphs of some indicators or parameters involved with active auscultation. The information in FIGS. 3A and 3B is measured, whereas the information in FIGS. 3C and 3D is derived. FIG. 3A is an exemplary chart of amplitude as a function of frequency. FIG. 3C is an exemplary chart of attenuation as a function of frequency, which is derived from frequency and amplitude data such as that shown in FIG. 3A. FIG. 3B is an exemplary chart of phase as a function of frequency, and FIG. 3D is a chart of velocity as a function of frequency, which is derived from the frequency and phase information such as that shown in FIG. 3B.

Active auscultation can be used to assist in diagnosing lung disease (also referred to herein as a condition) wherein again, a sound is introduced to the thorax such that it travels from one side of the thorax, through the lung, to another side of the thorax. The sound velocity and preferably attenuation which is measured is then compared with that of a normal, healthy lung. Since lung disease often manifests in reduced lung volume, a comparison can be used, again, to provide an indication as to whether a subject's lung exhibits a propensity for lung disease. Common lung diseases may include emphysema, asthma, regional collapse (atelectasis), interstitial oedema and both focal lung disease (e.g. tumour) and global lung disease (e.g. emphysema).

Passive Auscultation

The term "passive auscultation" generally refers to monitoring and/or receiving at least one naturally occurring sound from the body or a portion thereof for use in the diagnosis and/or treatment of the body or a portion thereof. In relation to the lungs, passive auscultation generally includes monitoring naturally occurring breath sounds, i.e. sounds associated with the patient's breathing. This is in contrast to the active auscultation described above where a signal is injected and then received. The breath sounds are monitored and processed with system 100's receiving unit 116 and control unit 110.

Passive auscultation provides very important information that a physician can use in understanding the condition of a patient's lungs. Passive auscultation is well accepted by physicians and provides valuable information that cannot be had via active auscultation techniques. However, because it has been difficult to quantify and lends itself more to subjective rather than objective analysis, more attention has recently been focused on the technique of active auscultation. This however, leaves out an important piece of the puzzle that a physician may use to arrive at a fully informed conclusion. System 100 utilizes both active and passive auscultation data.

FIG. 4 is a chart of breath sounds. The acoustic characteristics of these sounds are recognized by control unit 110. Therefore, by monitoring these breath sounds during passive auscultation, the system will have indications of the associated condition of the lung. An adventitious sound from the passive auscultation, when combined with an indicator from the active auscultation may point the physician to a more narrow range of possibilities and lead to a more accurate diagnosis. Likewise, a normal sound heard during passive auscultation may lead to a different range of possibilities of lung condition than would be foreseen from an adventitious sound or from active auscultation alone.

Adventitious lung sounds may be classified into three major categories: crackles (or rales), which are discontinuous (i.e., interrupted) sounds, and wheezes and rhonchi, which are continuous. Crackles may be further classified depending on their frequency, characteristics and amplitude. Wheezes may be similarly classified. An experienced and knowledgeable health care professional may also be able to diagnose certain pulmonary diseases, such as pneumonia, asthma, etc., simply by detecting, identifying and noting the location of particular adventitious lung sounds. This can be done with the aid of system 100 of the present invention.

Wheezing is a commonly used acoustical term in respiratory medicine. Wheezes are well understood to be an indicator of airway obstruction in infants, as a parameter to gauge the severity of asthma, or as a classifier in epidemiologic surveys, to name just a few examples. As can be seen in the chart of FIG. 4, a wheeze has the acoustic characteristic of a sinusoid with a range of about 100 to above 1000 Hz and a duration typically, but not necessarily, longer than 80 milliseconds. Generally speaking, a wheeze is indicative of an airway obstruction or flow limitation. Wheezes are "continuous" since their duration is much longer than that of "discontinuous" crackles. In most cases they do not extend more than 250 ms, but they will typically be longer than 80 to 100 ms. Their frequency range extends from less than 100 Hz to more than 1 kHz, and higher frequencies may be measured inside the airways.

Spontaneous wheeze is often present during inspiration in adults and children with asthma, but is not present in healthy subjects. Regional flow limitation during inspiration is a possibility but has not been proven. The sound of wheezing is easily recognized since it stands out from the noise of normal lung sounds. A wheeze of at least moderate intensity is characterized by sharp peaks in the power spectrum of respiratory sounds. Detection is possible with control unit 110 by comparing these spectral peaks to the average lung sound amplitude.

In addition to determining wheeze amplitude (i.e. the sound strength of the wheeze), the relative duration of wheezing, or "wheeze rate" is a recognizable parameter for determining the severity of flow limitation in a subject. The "wheeze rate" can be easily calculated after detecting wheezes with control unit 110, by dividing the time duration of the detected wheezes by the total time duration. Wheeze rates may further be classified as "Inspiratory" and "Expiratory" wheeze rates, according to the breath phases in which the wheezes appear.

In addition to the three major categories of adventitious lung sounds referenced above, whistles are also present in some conditions. A whistle is similar to a wheeze and is acoustically characterized by a sinusoid signal with a rapidly changing tone (frequency). Similar to wheezes, whistles are "continuous" and are typically longer than 80 ms in duration. The base frequency of a whistle is usually higher than that of a wheeze, usually being no less than 1200 Hz. A whistle is also indicative of airflow limitation. A "whistle rate" can be calculated in the same manner as "wheeze rate", i.e. by dividing the time duration of detected whistles by the total time duration. Similarly, whistle rates can be determined separately for inspiratory and expiratory phases of breathing.

Figure 10:
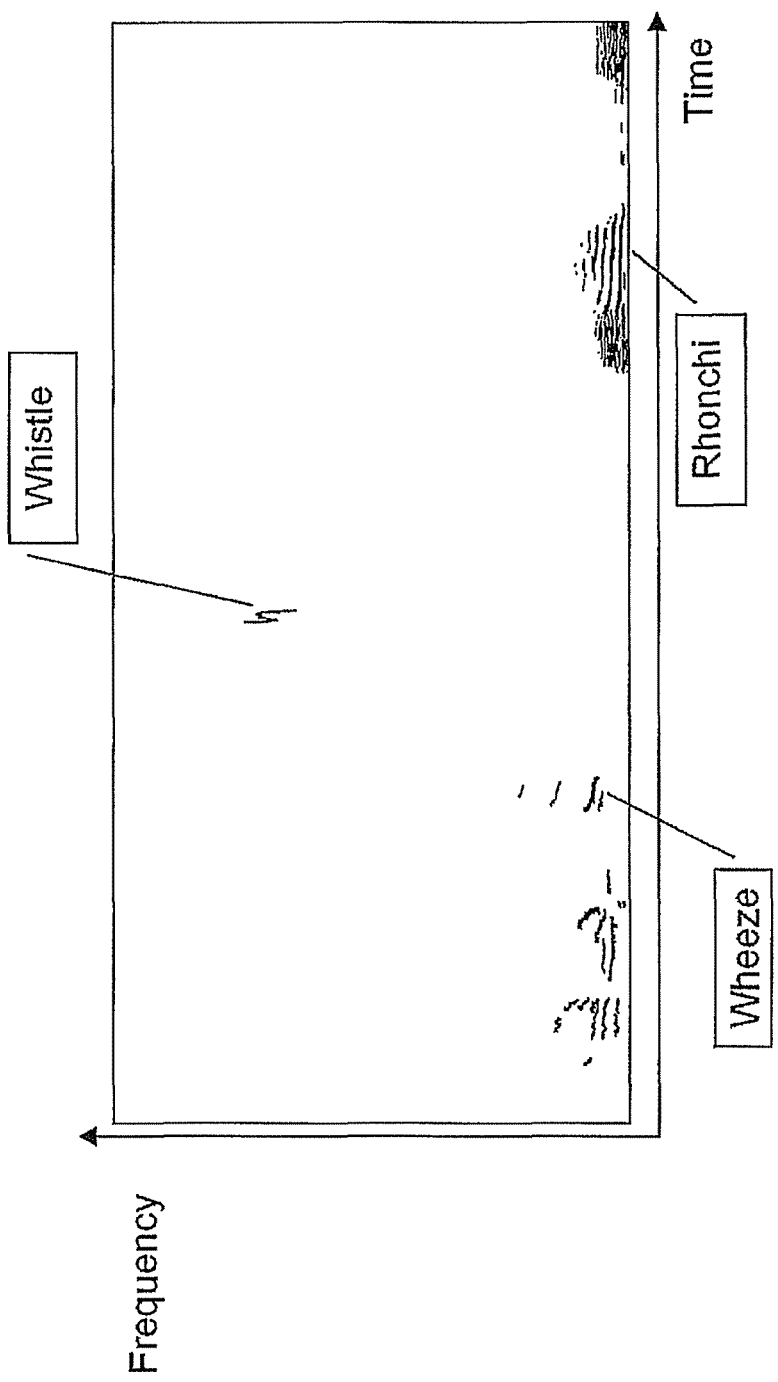
FIG. 10 is a frequency-time spectrograph showing adventitious respiratory sounds.

FIG. 10 is a frequency-time spectrograph showing a further example of adventitious respiratory sounds. Here, naturally occurring sounds associated with breathing and identified as "wheeze", a "whistle" and "rhonchi" are shown. These data associated with these sounds are combinable with other data obtained through active auscultation or active measurement of an introduced sound signal to determine a condition of a patient's lung.

Crackles are another type of easily recognizable adventitious lung sounds. Crackles have been characterized as "miniature explosions," and are heard much more frequently during inspiration than during expiration. Crackles are sometime categorized as either fine or coarse crackles. As can be seen in the chart of FIG. 4 crackles have the acoustic characteristic of a rapidly dampened wave deflection with a duration typically but not necessarily less than 20 milliseconds. Generally speaking, a crackle may indicate an airway closure or some type of airway secretion.

It is now generally accepted that fine and coarse crackles are associated with different conditions and so have diagnostic importance. Crackles in patients with fibrotic lung diseases are generally shorter in duration and period than the coarse crackles of patients with pneumonia. The most commonly used indices are the time duration of the initial deflection and the first two cycles of the waveform.

Although crackle features and characteristics can be associated with certain diseases, only certain associations are currently well correlated enough to have clinical utility at the moment. This is expected to change over time. Those with established clinical utility appear to be: the presence or absence of crackles to distinguish pulmonary fibrosis (crackles usually prominent) from sarcoidosis (crackles usually minimal or absent); fine, late inspiratory crackles indicating fibrotic lung disease and early, coarse crackles indicating obstructive lung disease; crackles as an early (perhaps first) sign of asbestosis, and crackles indicating heart failure.

A rhonchus is similar to a crackle and is acoustically characterized by a series of rapidly dampened sinusoids typically from less than 300 Hz in frequency and with a duration greater than 100 milliseconds. A rhoncus is generally indicative a secretions or abnormal airway collapsibility.

For more information on these conditions please refer to "Respiratory Sounds Advances Beyond the Stethoscope" by Pasterkamp et al., Am. J. Respir. Crit. Care Med., Volume 156, Number 3, September 1997, 974-987, which is hereby incorporated by this reference in its entirety.

Note that these characteristics and ranges obviously vary from patient to patient and are only given as example ranges, and should not be interpreted as limitations to the invention in any way.

Figure 5B:
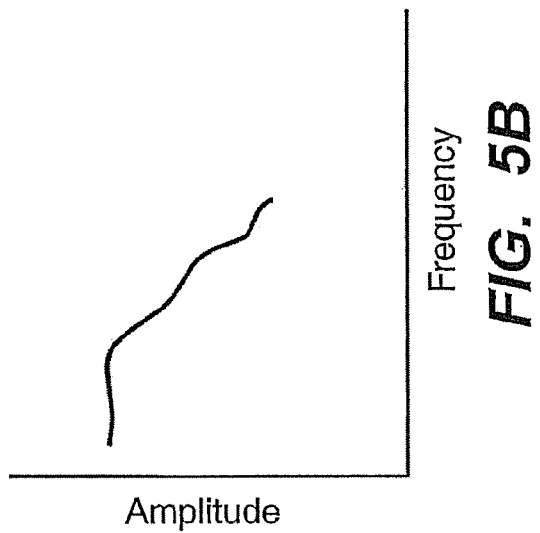
FIGS. 5A-5C are graphs of signals associated with passive auscultation.
Figure 5C:
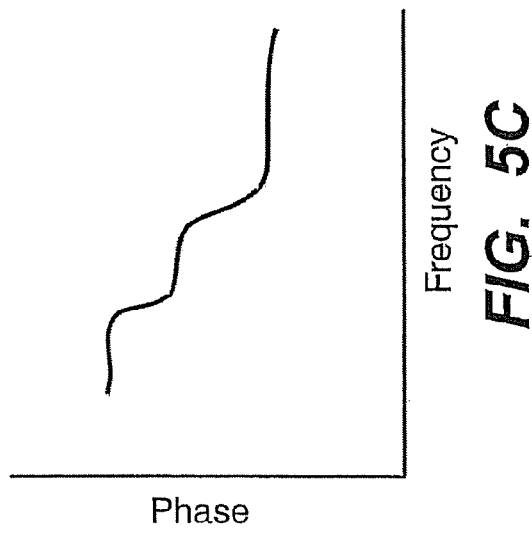
Figure 5A:

FIGS. 5A-5C are a few exemplary charts of some indicators or variables of passive auscultation. FIG. 5A shows amplitude of the monitored breath sounds as a function of time. A Fast Fourier Transform or FFT extracts such information as seen in FIGS. 5B and 5C. FIG. 5B shows amplitude as a function of time, and FIG. 5C shows phase as a function of frequency.

The present invention utilizes indications from both active and passive auscultation to arrive at a more informed conclusion. By combining or "multiplexing" lung condition indicators gathered from both of these different techniques, a more narrow set of indicators of lung condition is available. In the hands of a trained physician or other professional, this will increase the probability of more accurate diagnoses. System 100, and in particular, control unit 110 processes the signal received from monitored breath sounds (i.e. sounds associated with breathing) of passive auscultation as well as the signal introduced and then received by way of active auscultation. The system may perform multivariable analysis using variables obtained from both the passive and active measurements. Such analysis is well understood by those of skill in the art. The number of variables or condition indicators that can be utilized in such an analysis is very large. Depicting even a three dimensional analysis on (2 dimensional) paper is complex. The conditions, condition indicators, and characteristics that can be determined with the present invention include those earlier described and the following: early stage emphysema; late stage emphysema; chronic bronchitis; asthma; tissue micro-structure; alveolar dimensions; fenestrae size; airway mucus loading; and lung viscosity. This is not meant to be an exhaustive list and it is to be understood that with further study various combinations of measured and derived parameters will likely be associated with different conditions, condition indicators, and characteristics of the lung.

A few of the variables or indicators that have been previously described above are illustrated in FIGS. 6-9.

Figure 6:
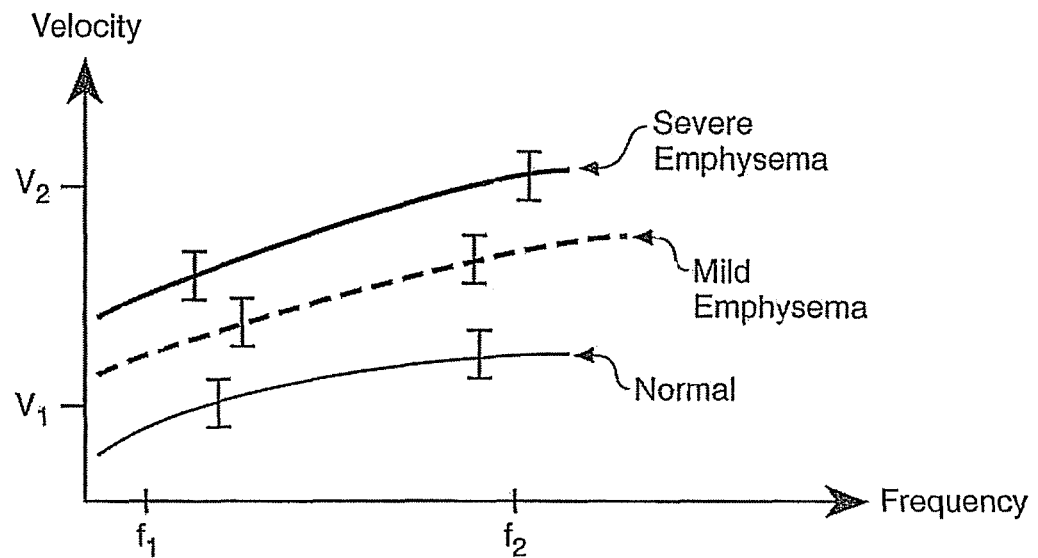
FIG. 6 is a graph of velocity as a function of frequency.

FIG. 6 illustrates velocity as a function of frequency, which is determined from active auscultation. Three curves and the associated error bars are shown illustrating the regions where these variables would indicate the lung condition as either normal lung function, mild emphysema, or severe emphysema. As was discussed at length previously, the higher the velocity of the introduced signal (along the frequency spectrum) the greater the indication of emphysema.

Figure 7:
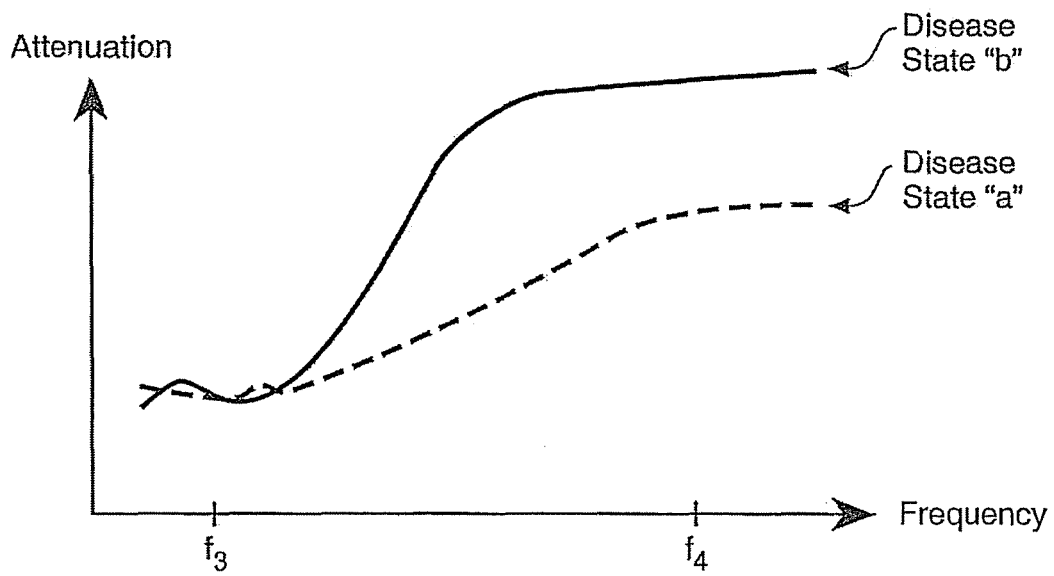
FIG. 7 is a graph of attenuation as a function of frequency and disease states that may be indicated.

FIG. 7 illustrates attenuation as a function of frequency. The attenuation-frequency curve provides an indication of one or more lung conditions. FIG. 7 illustrates attenuation at a different range of frequencies ($f_3$ and $f_4$) than in FIG. 6, but it should be understood that attenuation may also provide useful information when determined in the same range as velocity shown in FIG. 6. Different attenuation curves may indicate a different disease state. For example, the solid curve is shown to be indicative of "disease state b" whereas the dotted curve is shown to be indicative of "disease state a."

Figure 8:
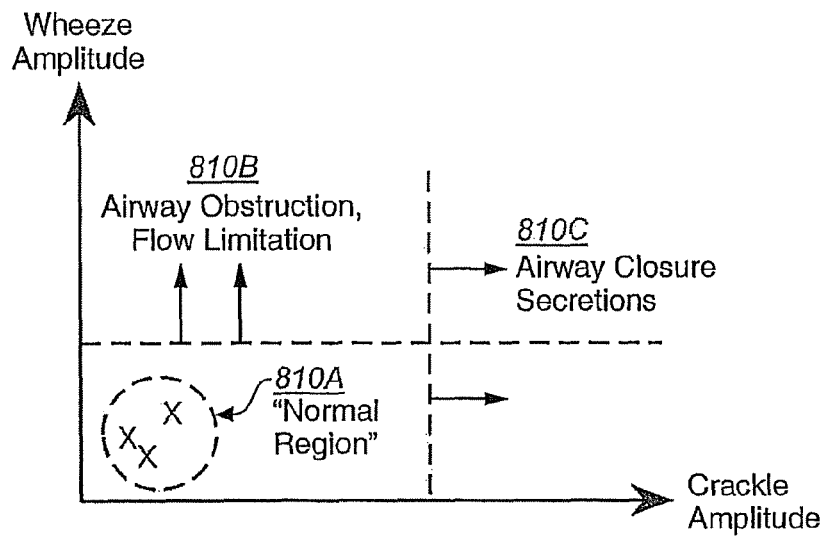
FIG. 8 is a graph of wheeze amplitude as a function of crackle amplitude.

FIG. 8 is a chart illustrating conditions associated with crackle amplitude and wheeze amplitude. There exists a region where both the wheeze amplitude and crackle amplitude are low, therefore indicating a healthy lung. This is signified by "Normal Region" 810A. A high wheeze amplitude may indicate an airway obstruction or flow limitation, as is represented by region 810B, the region above the horizontal dotted line. Also, a relatively high crackle amplitude is indicative of an airway closure or secretions, as is represented by region 810C, the region to the right of the vertical dotted line.

Figure 9:
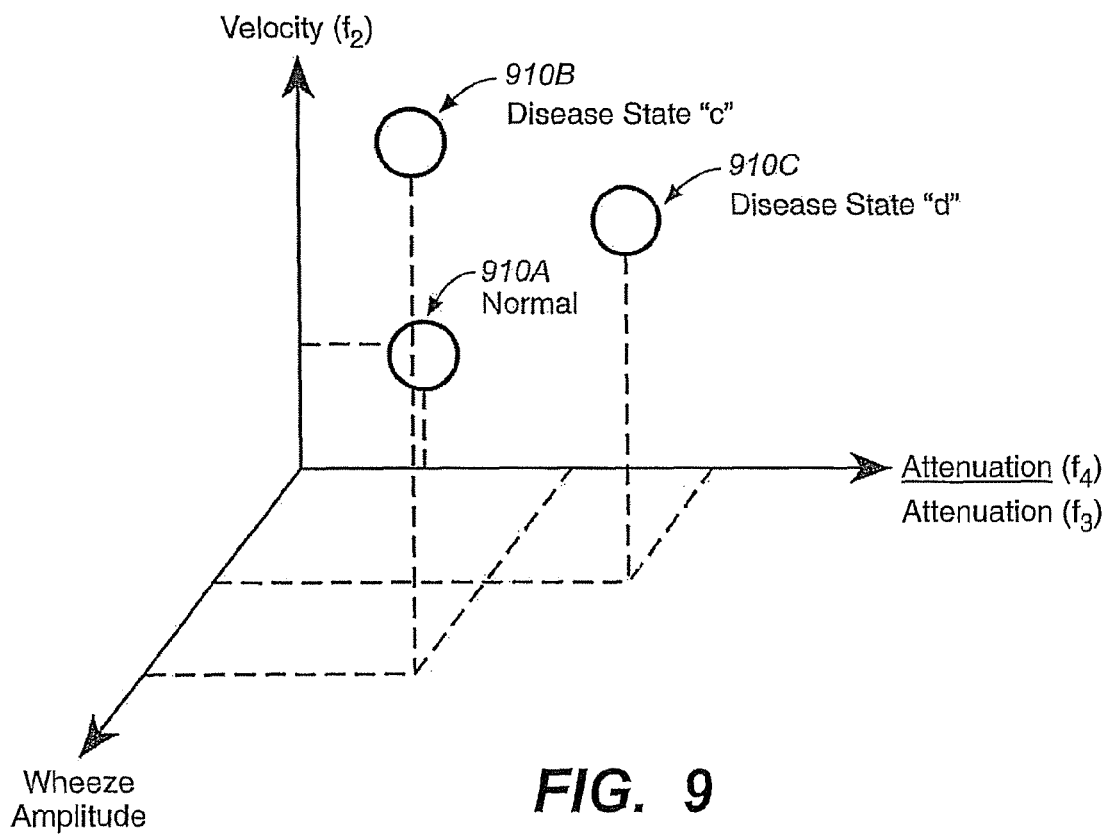
FIG. 9 is a three dimensional representation of the multi-dimensional analysis of the present invention.

As mentioned previously a large number of variables can be combined in a multi-variable or multi-dimensional analysis. This may include tens or hundreds of variables, but all that can be represented on paper are two or three variables. FIG. 9 is an example of a three dimensional analysis although higher dimension analysis is preferable. Different lung states may be indicated according to the levels of the various indicators. In this case, the indicators include wheeze amplitude, velocity, and attenuation. The attenuation is a ratio of the attenuation at different frequencies, for example the ratio of attenuation at frequency 4 versus frequency 3.

A relatively low wheeze amplitude, velocity, and attenuation ratio are indicative of normal lung function, as represented by normal region 910A. A high velocity with little wheeze amplitude and moderate attenuation ratio may together indicate "disease state c." Similarly, a moderate wheeze amplitude together with a relatively high velocity and attenuation ratio may point to "disease state d."

While active auscultation provides excellent hard data, a physician or other professional benefits from having as much data as possible in any analysis. Combining information from both active and passive auscultation, as is done in the present invention, is far more beneficial than a conclusion based upon data from only one or the other methods. This is especially true when a microprocessor driven control system aids in the analysis as is the case with the present invention.

The present invention is described herein with reference to the accompanying examples and figures. It is to be understood that the description is illustrative only and should not be taken to be limiting in any way, or as a restriction on the generality of applications for the invention previously described. Although the various aspects and features of the present invention have been described with respect to various embodiments and specific examples herein, it will be understood that the invention is entitled to protection within the full scope of the appended claims.

The invention claimed is:

1. A method of determining a condition of at least one lung of a patient comprising:
    making an active measurement of the at least one lung by non-invasively introducing a signal through contact with a thoracic skin surface of the patient from a transducer comprising one or more audible frequencies into the at least one lung and receiving the at least one audible frequency signal during or upon passage through the at least one lung;
    making a passive measurement of the at least one lung by receiving at least one naturally occurring sound associated with breathing by the patient; and
    determining a condition of the at least one lung by combining data associated with the active measurement with data associated with the passive measurement.

2. The method of claim 1 wherein making an active measurement further includes determining one or more variables from the received signal.

3. The method of claim 2 wherein one variable of the one or more variables is the velocity of the received signal.

4. The method of claim 3 wherein the velocity is determined over a range of frequencies associated with the audible frequency signal.

5. The method of claim 2 wherein one variable of the one or more variables is the phase of the received signal.

6. The method of claim 2 wherein one variable of the one or more variables is the dispersion of frequencies of the received signal over a range of frequencies.

7. The method according to claim 1 further comprising ceasing to introduce a sound signal having one or more audible frequencies while making a passive measurement of the at least one lung.

8. The method according to claim 1 wherein the data comprises a ratio of an amplitude of the received audible frequency signal at a first frequency versus the amplitude of the received audible frequency signal at a second frequency.

9. The method according to claim 1 wherein the data comprises a ratio of a velocity of the received signal at a first frequency versus a velocity of the received signal at a second frequency.

10. The method according to claim 1 wherein the data comprises a ratio of an attenuation of the received signal at a first frequency versus the attenuation of the received signal at a second frequency.

11. A method of determining the condition of a patient's lung, the method including the steps of:
    injecting a signal comprising audible frequencies through the patient's lung via a thoracic skin surface;
    recording the injected signal after the injected signal has passed through the patient's lung and processing the signal to determine a first set of criteria indicative of a condition of the lung;
    monitoring naturally occurring breath sounds of the patient's lung;
    processing the breath sounds of the patient's lung to determine a second set of criteria indicative of a condition of the lung; and
    narrowing the number of criteria indicative of a condition of the lung by comparing the first set of criteria from the injected signal with the second set of criteria from the naturally occurring breath sounds.

12. The method of claim 11 wherein the first set of criteria is selected from a group comprising a cross-correlation function, a coherence function and a transfer function.

13. The method of claim 11 wherein the second set of criteria is selected from a group comprising one or more of wheeze rate, wheeze amplitude, rhonchi rate, rhonchi amplitude, whistle rate, whistle amplitude, crackle rate and crackle amplitude.

14. The method of claim 11 wherein recording the injected signal includes receiving the injected signal with one or more transducers.

15. The method of claim 11 wherein monitoring the naturally occurring breath sounds includes monitoring one or more transducers.

16. The method of claim 11 wherein injecting the signal does not occur at the same time as monitoring the naturally occurring breath sounds.

17. Apparatus for evaluating the condition of a lung of a patient, the apparatus comprising:
    one or more emitting transducers introducing a signal to a thoracic skin surface of the patient wherein the signal comprises audible frequencies into the lung;
    one or more receiving transducers that receive the introduced signal after it has passed through at least part of the lung; and
    a processing unit that
        monitors the received signal and determines a first set of indicators of a condition of the lung based on the received signal, and
        monitors one or more naturally occurring sounds associated with breathing by the patient and determines a second set of indicators of a condition of the lung based on the one or more monitored naturally occurring sounds, and
        compares the first and second set of indicators, and provides a third set of indicators corresponding to a portion of overlap of the first and second sets of indicators respectively, the third set of indicators being indicators of lung condition based upon both the introduced signal and the naturally occurring sounds.

18. Apparatus according to claim 17 wherein the one or more receiving transducers also monitor naturally occurring sounds associated with breathing by the patient.

19. Apparatus according to claim 18 configured to cease introduction of sound during monitoring of naturally occurring sounds associated with breathing by the patient.

* * * * *